(12) United States Patent
Melozzi

(10) Patent No.: US 10,603,048 B2
(45) Date of Patent: Mar. 31, 2020

(54) LAMINECTOMY FORCEPS WITH IMPROVED LEVER MECHANISM

(71) Applicant: Alessandro Melozzi, Teramo (IT)

(72) Inventor: Alessandro Melozzi, Teramo (IT)

(*) Notice: Subject to any disclaimer, the term of this patent is extended or adjusted under 35 U.S.C. 154(b) by 108 days.

(21) Appl. No.: 15/769,636

(22) PCT Filed: Oct. 27, 2016

(86) PCT No.: PCT/EP2016/075918
§ 371 (c)(1),
(2) Date: Apr. 19, 2018

(87) PCT Pub. No.: WO2017/072224
PCT Pub. Date: May 4, 2017

(65) Prior Publication Data
US 2018/0280034 A1    Oct. 4, 2018

(30) Foreign Application Priority Data

Oct. 29, 2015   (IT) .................. 102015000067052

(51) Int. Cl.
*A61B 17/16* (2006.01)
*A61B 17/29* (2006.01)
*A61B 17/00* (2006.01)

(52) U.S. Cl.
CPC ...... *A61B 17/1611* (2013.01); *A61B 17/1671* (2013.01); *A61B 17/2909* (2013.01); *A61B 2017/0046* (2013.01); *A61B 2017/292* (2013.01); *A61B 2017/2912* (2013.01); *A61B 2017/2919* (2013.01)

(58) Field of Classification Search
CPC ............ A61B 17/1611; A61B 17/1671; A61B 17/2909; A61B 2017/0046; A61B 2017/2912; A61B 2017/2919; A61B 2017/292
See application file for complete search history.

(56) References Cited

U.S. PATENT DOCUMENTS

| | | | |
|---|---|---|---|
| 5,928,252 A * | 7/1999 | Steadman | A61B 17/0482 606/139 |
| 2009/0048625 A1* | 2/2009 | Pedersen | A61B 17/2909 606/205 |
| 2011/0071563 A1* | 3/2011 | Magliani | A61B 17/1611 606/205 |

* cited by examiner

*Primary Examiner* — Jocelin C Tanner

(57) ABSTRACT

A laminectomy forceps having a cutting unit with a fixed beak and a sliding tray slidingly mounted on the fixed beak, an actuation lever to actuate the sliding tray, a handle in opposed position to the actuation lever and joined to an external frame joined to the fixed beak, a lever mechanism connected to the actuation lever and to the sliding tray, the lever mechanism including a first lever shaped as a straight bar, a second lever shaped as a straight bar and having a first arm between a fulcrum and a first end and a second arm between the fulcrum and a second end and a third lever shaped as a straight bar connected to a stem intended to push the sliding tray.

12 Claims, 11 Drawing Sheets

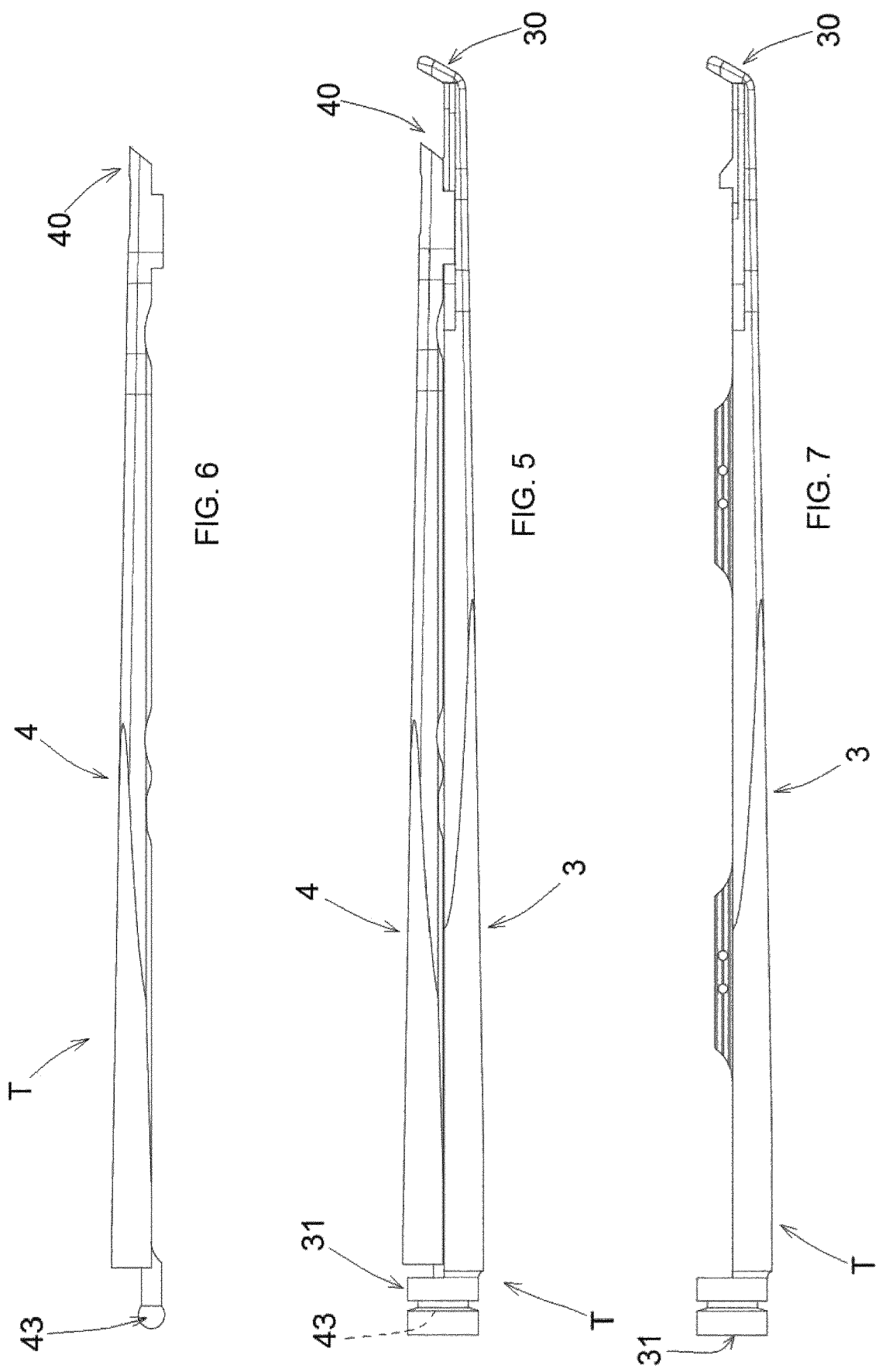

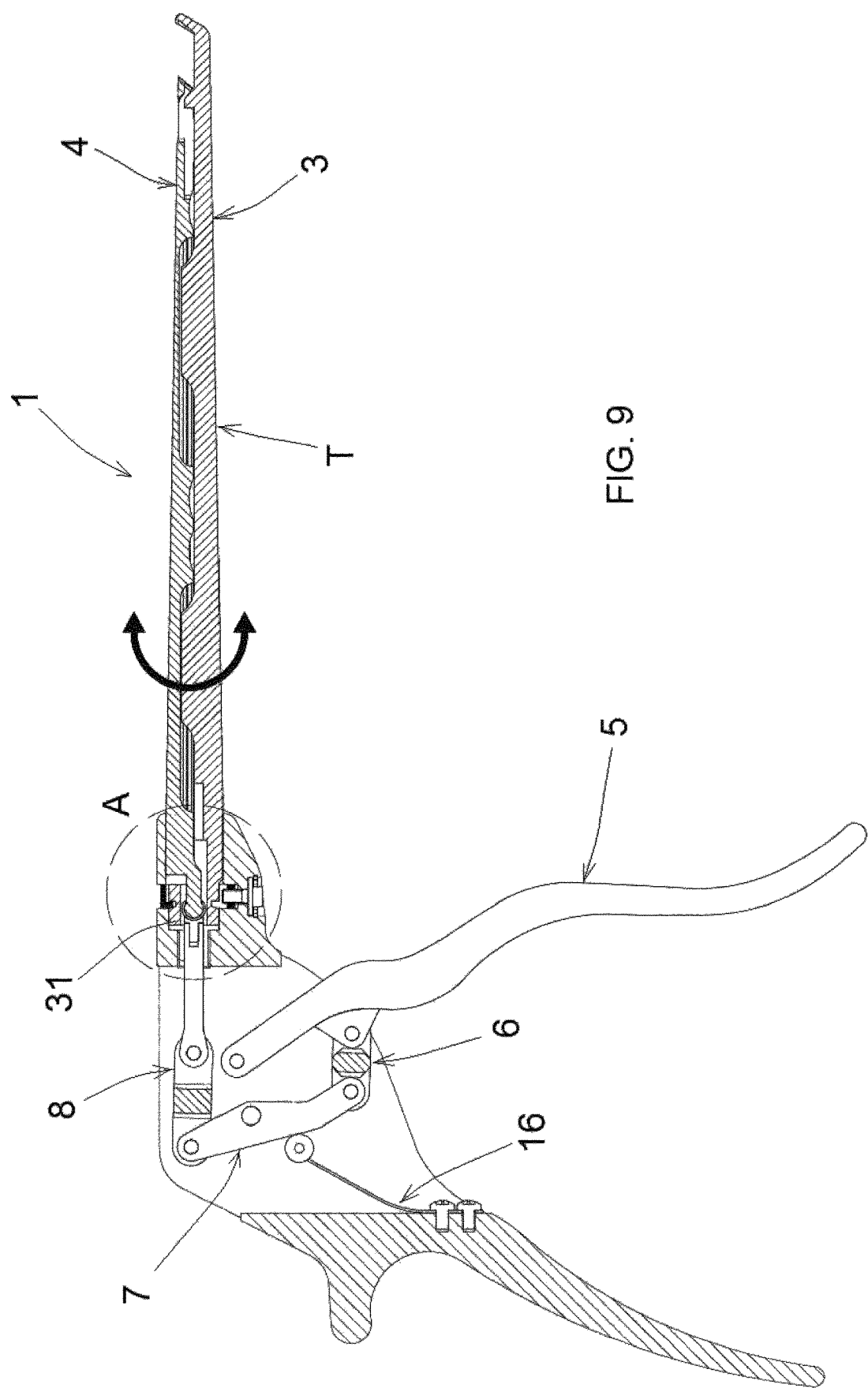

LAMINECTOMY FORCEPS WITH IMPROVED LEVER MECHANISM

The present invention relates to a laminectomy forceps. Laminectomy is a surgical operation that consists in excising the posterior arch of a vertebra by totally or partially removing one or more vertebral laminae and consequently opening a vertebral channel. During a laminectomy operation the surgeon removes bone fragments with a forceps.

EP2326262 B1 discloses a laminectomy forceps comprising:
- a handle joined to a fixed beak,
- a sliding tray slidingly mounted on the fixed beak and ending with a cutting end, and
- an actuation lever in opposite position to the handle and connected to the sliding tray in order to actuate the sliding tray.

The fixed beak is provided with a cutting backing end that acts as stop surface for the cutting end of the tray in such manner to generate a cutting area.

Moreover the forceps comprises a force multiplier lever mechanism disposed between the actuation lever and the sliding tray. The force multiplier lever mechanism comprises a plurality of levers that are articulated in such a way that the actuation lever determines the sliding of the sliding tray.

The force multiplier lever comprises a first L-shaped lever that is hinged to the handle and is arranged in such manner to be actuated by the actuation lever. The first L-shaped lever defines a longer portion configured to interact with the actuation lever and a shorter portion connected to a second lever.

The second lever is connected to the first L-shaped lever and is configured in such manner to be actuated with respect to the first L-shaped lever.

The force multiplier lever also comprises a third L-shaped lever that is connected to the second lever and is configured in such manner to be actuated with respect to the second lever. The third L-shaped lever is hinged to the handle and is arranged in such manner to actuate the sliding tray. In fact, the third L lever defines a longer portion connected to the sliding tray and a shorter portion connected to the second lever.

Although the levers described in EP2326262 B1 are arranged in such manner that the force multiplier lever mechanism multiplies the force exerted by a surgeon on the actuation lever and transmits the multiplied force to the tray, the L-shaped levers are difficult to make and to assembly, as well as provided with an excessive volume.

DE202005019304 U1 discloses a surgical forceps comprising a cutting unit comprising a fixed beak and a tray that is slidingly mounted on the fixed beak. The fixed beak comprises a stop end intended to act as stop for a cutting end of the sliding tray. The forceps comprises an actuation lever to actuate the sliding tray. A handle is joined to the fixed beak and opposed to the actuation lever. Moreover, the forceps comprises a lever mechanism connected to the actuation lever and to the handle in order to transmit the force exerted on the actuation lever and on the handle to the sliding tray and to the fixed beak.

Such a lever mechanism comprises:
- a first lever comprising a first end that is hinged to the actuation lever and a second end that is hinged to a second lever;
- a second lever shaped as a straight bar, comprising a first end that is connected to the first lever and a second end that is hinged to the sliding tray;
- a third lever shaped as a straight bar and comprising a first end that is hinged to the second lever and a second end that is hinged to the handle.

The second lever is directly connected to the sliding tray and is pivoted to the third lever in a central point. The third lever is connected to the fixed frame, meaning that the third lever is used to connect the second lever to the fixed frame. Given that the second lever is connected directly to the tray and the third lever is not connected to the tray, such a type of lever mechanism does not generate an efficient force multiplication.

The purpose of the present invention is to overcome the drawbacks of the prior art, by disclosing a laminectomy forceps that is resistant and simple to make and assemble.

An additional purpose is to disclose a laminectomy forceps that is reliable and inexpensive.

An additional purpose of the present invention is to disclose a lever mechanism that is able to ensure an effective and efficacious force multiplication.

These purposes are achieved according to the present invention with the characteristics of the independent claim 1.

Advantageous embodiments of the invention will appear from the dependent claims.

The laminectomy forceps according to the invention comprises a cutting unit comprising a fixed beak and a sliding tray slidingly mounted on the fixed beak. The fixed beak comprises a stop end intended to act as stop for a cutting end of the sliding tray.

Moreover the forceps comprises an actuation lever to actuate the sliding tray, a lever mechanism connected to the actuation lever and to the sliding tray to multiply the force impressed on the actuation lever and transmit the multiplied force to the sliding tray and a handle in opposite position to the actuation lever and joined to an external frame joined to the fixed beak.

The force multiplicator lever mechanism comprises:
- a first lever shaped as a straight bar and comprising a first end that is hinged to the actuation lever by means of a first pin and a second end that is hinged to the second lever by means of a second pin;
- a second lever shaped as a straight bar revolvingly mounted around a fulcrum fixed to the external frame in such a way to define:
  - a first arm between the fulcrum and a first end of the second lever that is connected to the first lever by means of a second pin and
  - a second arm between the fulcrum and a second end of the second lever that is hinged to the third lever by means of a third pin;
- a third lever shaped as a straight bar and comprising a first end that is hinged to the second lever by means of the third pin and a second end that is connected by means of a fourth pin to a stem intended to push the sliding tray.

In view of the above, it is evident that, being shaped as a straight bar, said levers are easy to make, inexpensive and resistant.

Moreover, the fact that the third lever is connected to the second lever and to the stem that pushes the sliding tray ensures a force multiplication during the actuation of the actuation lever.

For the sake of clarity, the description of the laminectomy forceps according to the invention continues with reference to the attached drawings, which have a merely illustrative, not limiting value, wherein:

FIG. 5 is a side view of a cutting unit of the forceps of FIG. 1;

FIGS. 6 are 7 are side views of parts of the cutting unit of FIG. 5;

FIG. 9 is the same view as FIG. 8, except for the fact that the adjustment means are shown in a position in which they allow for rotating the cutting unit;

Figure 1:
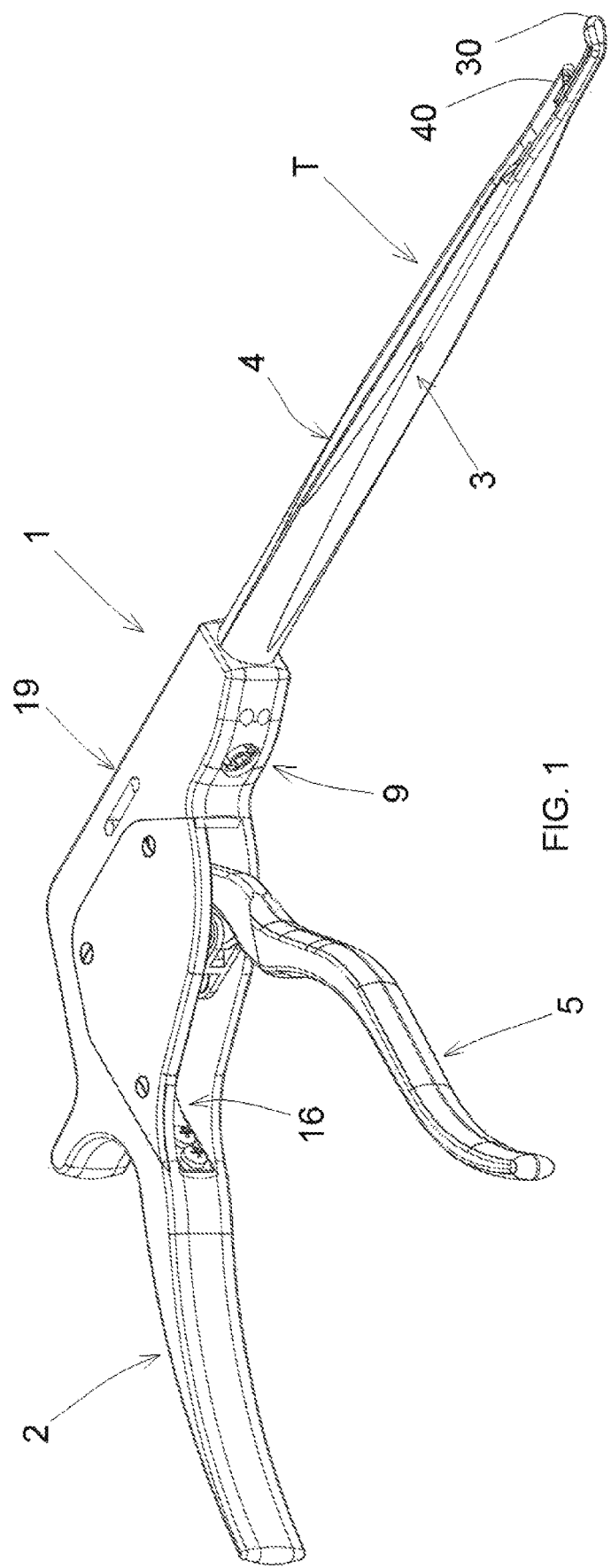
FIG. 1 is an axonometric view of a forceps according to the invention.

With reference to FIG. 1, a laminectomy forceps (1) is disclosed. The forceps (1) comprises a cutting unit (T) comprising a fixed beak (3) and a sliding tray (4) slidingly mounted on the fixed beak (3). The sliding tray (4) is actuated by an actuation lever (5). The actuation lever (5) is opposed to a handle (2). The surgeon rests the handle (2) on the palm of his or her hand and actuates the actuation lever (5) with the fingers of the same hand. The handle (2) is joined to an external frame (19) joined to the fixed beak (3).

The fixed beak (3) has a stop portion (30) and the sliding tray has a cutting portion (40). The stop portion (30) of the fixed beak acts as stop for the cutting portion (40) of the sliding tray (4), in such manner to generate the cutting area, wherein the surgeon places the part of the bone to be excised.

The cutting portion (40) and the stop portion (30) have opposed cutting borders. Therefore the forward movement of the cutting portion (40) of the sliding tray towards the stop portion (30) of the fixed beak cuts and excises the bone fragment disposed between the cutting portion (40) and the stop portion (30) by means of the cutting borders of the cutting unit (40) and of the stop portion (30) in opposite position.

Figure 2:
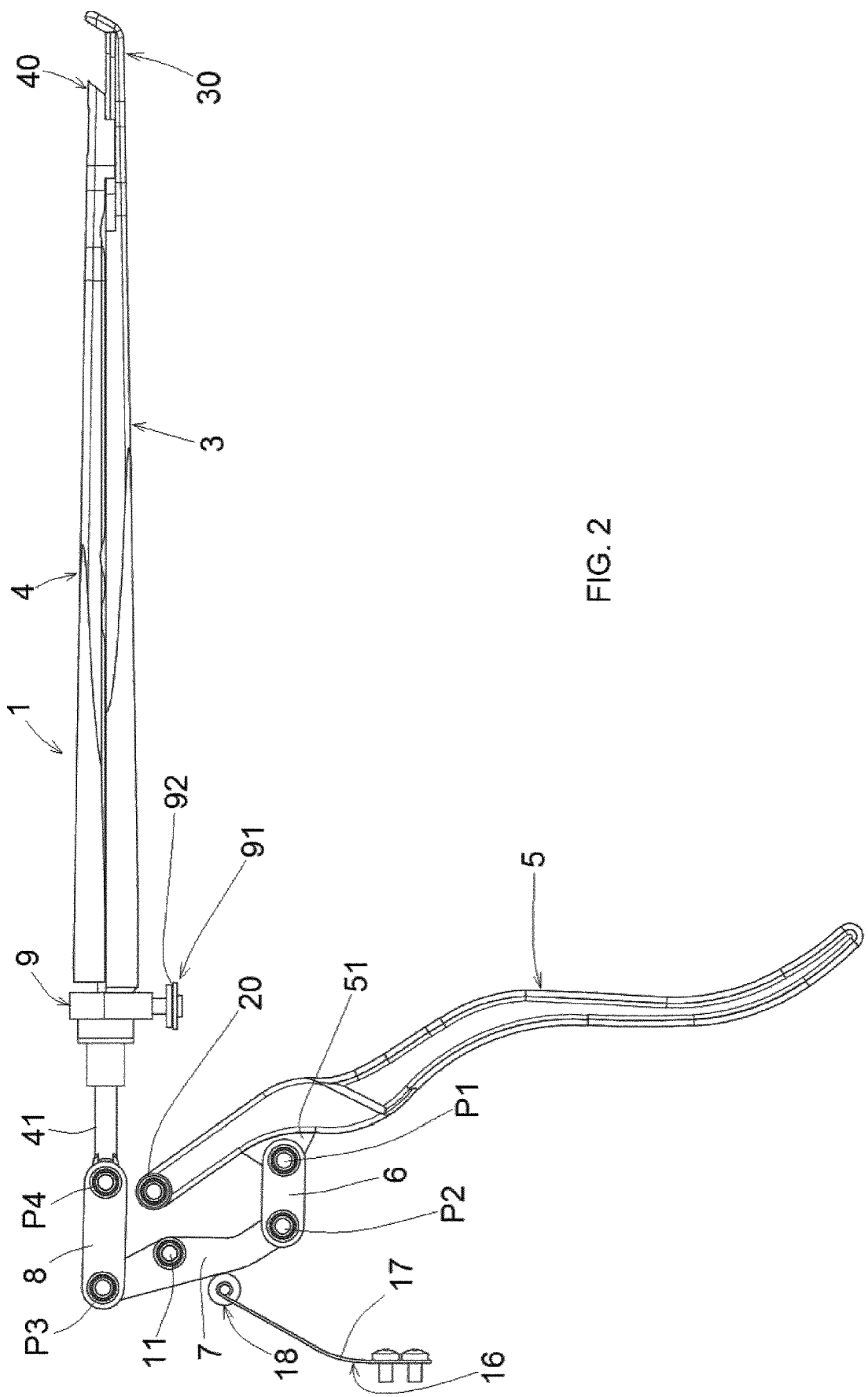
FIG. 2 is a side view of the forceps of FIG. 1, without the cover.
Figure 3:
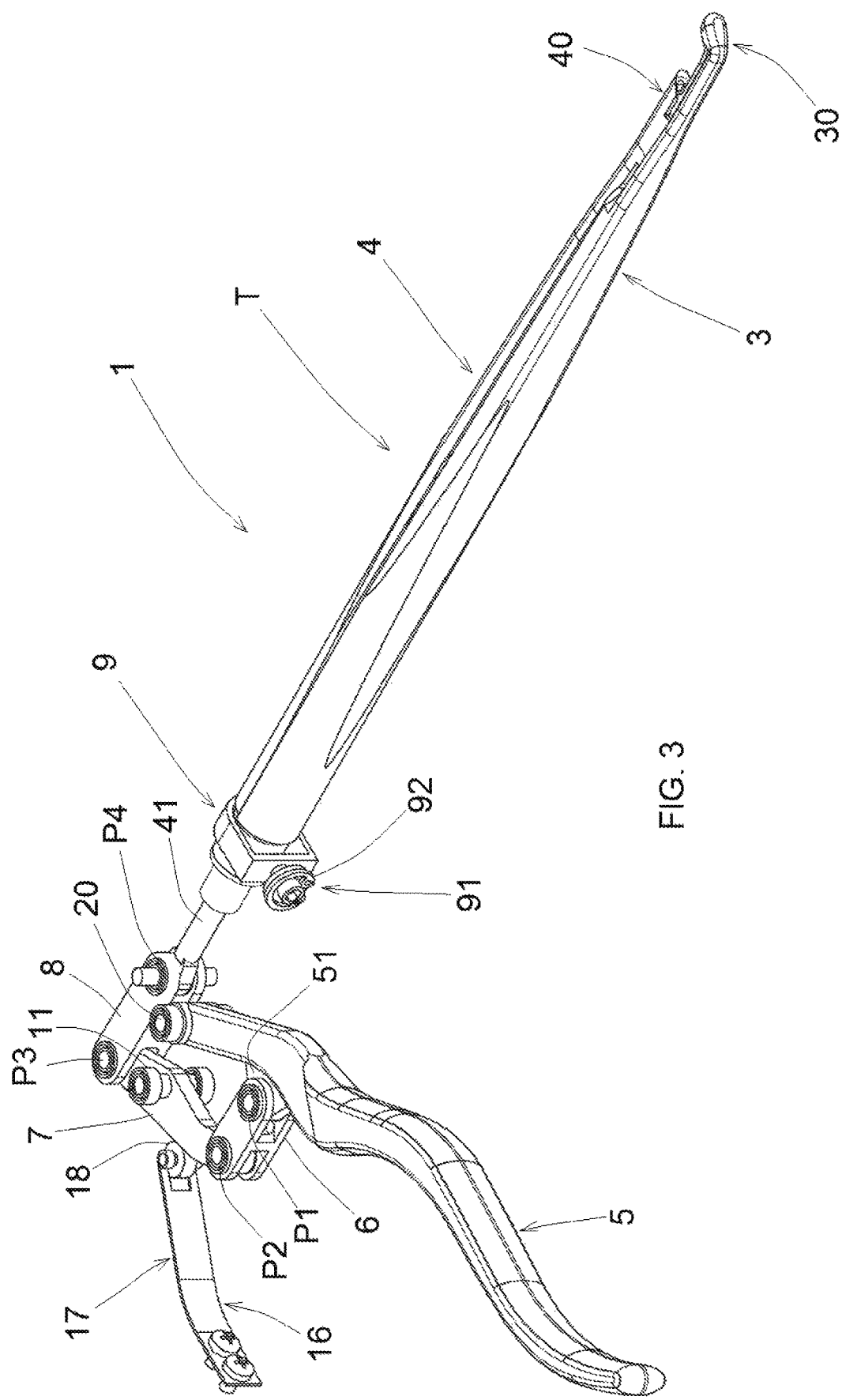
FIG. 3 is an axonometric view of FIG. 2.
Figure 4:
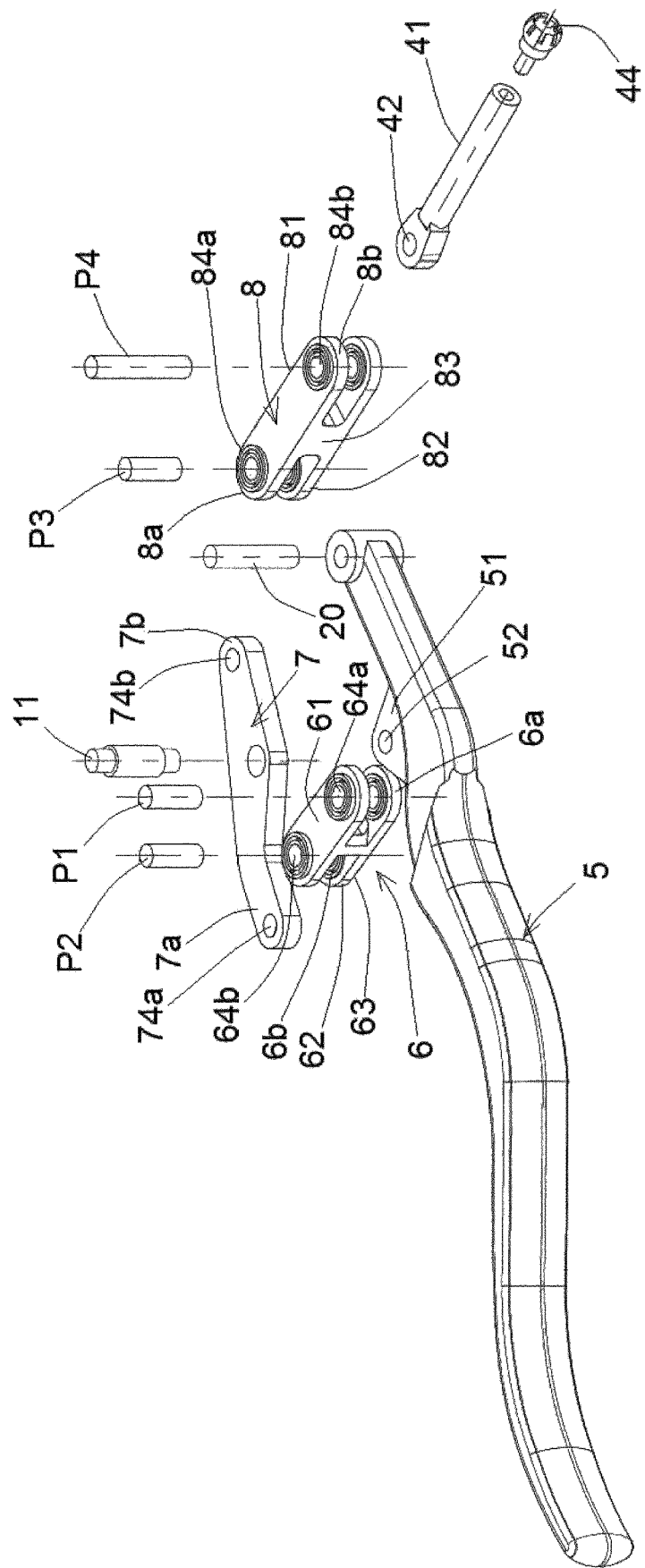
FIG. 4 is an exploded axonometric view of a lever mechanism of the forceps of FIG. 1.

With reference to FIGS. 2-4, the actuation lever (5) is connected to the sliding tray (4) by means of a lever mechanism that multiplies the force impressed by the surgeon on the actuation lever (5) and transmits the multiplied force to the sliding tray (4). The actuation lever (5) comprises a first free end and a second end that rotates around a pin (20) revolvingly connected to an external frame (19) (FIG. 1) joined to the handle (2).

The actuation lever (5) has wavy shape in such manner to be ergonomically comfortable for the surgeon, ensuring a good grip and reducing the fatigue on the surgeon's hand. The actuation lever (5) comprises a rigid wing (51) facing the handle (2) and comprising a through hole (52) for connecting the actuation lever to the lever mechanism.

The lever mechanism is composed by three levers:
a first lever (6) that is hinged to the actuation lever (5),
a second lever (7) that is hinged to the external frame (19), and
a third lever (8) that is hinged to the second lever and is connected to the sliding tray (4).

The first lever (6) is shaped as a straight bar and comprises a first end (6a) that is hinged to the actuation lever (5) by means of a first pin (P1) and a second end (6b) that is hinged to the second lever (7) by means of a second pin (P2). In this way, a movement of the actuation lever (5) will move the first lever (6) that in turn will move the second lever (7).

The first lever (6) has an "H"-shape in longitudinal section and comprises two external walls (61, 62) connected by a central rib (63) in such a way to define a first fork-shaped cavity in correspondence of the first end (6a) of the first lever and a second fork-shaped cavity in correspondence of the second end (6b) of the first lever. Each external wall (61, 62) of the first lever has a through hole (64a, 64b) in correspondence of each cavity of the first lever. The through holes (64a, 64b) ending on the same cavity are concentric.

The first cavity of the first lever is intended to house the wing (51) of the actuation lever (5) in such a way that the hole (52) of the wing of the actuation lever and the holes (64a) in correspondence of the first end are concentric. In view of the above, the first pin (P1) is inserted in the hole (52) of the actuation lever and in the holes (64a) in correspondence of the first end (6a) of the first lever in order to connect the first lever (6) to the actuation lever (5).

The second cavity of the first lever (6) is intended to house one end of the second lever (7).

The second lever (7) is a straight bar revolvingly mounted around a fulcrum (11) fixed to the external frame (19) in such way to define two arms. The second lever (7) comprises:
a first arm between the fulcrum (11) and a first end (7a) of the second lever connected to the first lever (6) by means of the second pin (P2) and
a second arm between the fulcrum (11) and a second end (7b) of the second lever hinged to the third lever (8) by means of a third pin (P3).

The first arm is longer than the second arm. The second lever (7) is longer than the first lever (6).

The first end (7a) of the second lever comprises a hole (74a) in concentric position with respect to the holes (64b) of the first lever, in correspondence of the second end (6b) of the first lever. In this way, the second pin (P2) is inserted into the hole (74a) of the second lever and in the holes (64a) of the first lever in correspondence of the second end (6a) of the first lever in order to connect the first lever (6) to the second lever (7).

The second end (7b) of the second lever comprises a hole (74b) for connection with the third lever (8).

The third lever (8) is shaped as a straight bar that is longer than the first lever (6) and shorter than the second lever (7).

The third lever (8) comprises a first end (8a) that is hinged to the second lever (7) by means of the third pin (P3) and a second end (8b) that is connected by means of a fourth pin (P4) to a stem (41) intended to push the sliding tray (4).

The third lever (8) has an "H"-shaped longitudinal section and comprises two external walls (81, 82) connected by a central rib (83) in such a way to define a first fork-shaped cavity in correspondence of the first end (8a) and a second fork-shaped cavity in correspondence of the second end (8b).

Each external wall (81, 82) of the third lever comprises a through hole (84a, 84b), in correspondence of each cavity. The first cavity of the third lever is intended to house the second end (7b) of the second lever (7), in such a way that the hole (74b) of the second end of the second lever and the holes (84a) in correspondence of the first end (8a) of the third lever are concentric. In view of the above, the third pin (P3) is inserted in the hole (74b) of the second lever (7) in correspondence of the second end (7b) of the second lever and in the holes (84a) of the third lever in correspondence of the first end (8a) of the third lever in order to connect the second lever (7) to the third lever (8). The second cavity of the third lever houses the stem (41) that is connected to the sliding tray (4).

The stem (41) comprises a first end comprising a hole (42) in concentric position with respect to the holes (84b) of the third lever in correspondence of the second end (8b) and a second end fixed to the sliding tray (4). The fourth pin (P4) passes through the hole (42) of the stem (41) and the holes (84b) of the third lever in correspondence of the second end (8b) in order to connect the third lever (8) to the stem (4) that pushes the sliding tray (4). In this way, the sliding tray (4) can only slide forward and backward on the fixed beak (3).

The actuation lever (5) can move with respect to the handle (2) from an opening position, wherein the actuation lever is far apart from the handle and the cutting portion (40) of the sliding tray is far apart from the stop portion (30) of the fixed beak, to a closing position, wherein the actuation lever is proximal to the handle and the cutting portion (40) of the sliding tray is stopped against the stop portion (30) of the fixed beak.

With reference to FIG. 2, when the actuation lever (5) is in opening position, a first obtuse angle ($\alpha$) of approximately 95°-110° is formed between the first lever (6) and the second lever (7); whereas a second acute angle ($\beta$) of approximately 50°-70° is formed between the second lever (7) and the third lever (8).

While the actuation lever (5) is gradually actuated, the first angle ($\alpha$) is reduced until it becomes an acute angle of approximately 50°-70°; whereas, the second angle ($\beta$) increases until it becomes an obtuse angle of approximately 95°-110°. This variation of the first and of the second angle ($\alpha, \beta$) during the travel of the actuation lever (5) from the opening position to the closing position acts as force multiplicator. In view of the above, at the beginning of the travel of the actuation lever (5) (when the bone is not be cut), large displacements of the sliding tray (4) are obtained for small displacements of the actuation lever (5). On the contrary, at the end of the travel of the actuation lever (5) (when the bone is to be cut), small displacements of the sliding tray (4) are obtained for large displacements of the actuation lever (5), in such manner to reduce the force to be exerted by the surgeon on the actuation lever (5) in order to cut the bone.

The forceps (1) also comprises automatic return means (16) intended to maintain the actuation lever (5) in opening position. In particular, said automatic return means (16) comprise an elastic plate (17) acting as leaf spring or beam spring, which is loaded when the actuation lever (5) is moved manually towards the handle, i.e. from the opening position to the closing position. When the surgeon releases the actuation lever (5), the elastic plate (17) is unloaded, pushing the actuation lever (5) to the opening position. In fact, the elastic plate (17) stresses the actuation lever (5) to move away from the handle (2) when the surgeon releases the actuation lever (5).

The elastic plate (17) comprises a first end that is fixed to the handle (2) and a second end that is connected to a wheel (18). The wheel (18) is intended to slide on the second lever (7) in such manner that when the first arm of the second lever (7) is moved towards the handle (5) and the second arm of the second lever (7) rotates towards the actuation lever (5), the elastic plate (17) is loaded. Then, as soon as the surgeon releases the actuation lever (5), the elastic plate (17) is unloaded, pushing the first arm of the second lever towards the actuation lever. Consequently, also the first lever (6) moves away from the handle (2), moving the actuation lever (5) away from the handle (2).

As shown in FIGS. 5, 6 and 7, the fixed beak (3) comprises a proximal end portion (31) with a circular shape in cross-section, which is intended to be removably fixed to a connector (9) (FIG. 3) joined to the fixed frame (19) in such a way that the cutting unit (T) can be released from the fixed frame (19).

The proximal end portion (31) of the fixed beak houses a proximal end portion (43) of the sliding tray (4). The proximal end portion (43) of the sliding tray (4) is intended to be fixed to the stem (41). In fact, the second end of the stem (41) comprises a spherical housing (44) (FIG. 4) and the proximal end portion (43) is a sphere intended to be removably fixed to the stem (41) connected to the lever mechanism, forming an omnidirectional spherical joint.

In this way, when the stem (41) is pushed towards the sliding tray (4), it consequently pushes the sliding tray (4) towards the stop portion (30) of the fixed beak.

As shown in FIG. 2, the proximal end portion (31) of the fixed beak is intended to be inserted inside the connector (9) fixed to the external frame (19) in correspondence of the stem (41), in such a way that:
   the sliding tray (4) can be fixed to the stem (41) in order to be moved by means of the lever mechanism, and
   the fixed beak (3) can be fixed to the connector (9) and joined to the external frame (19) and to the handle (2).

As shown in FIGS. 2 and 3, the forceps (1) comprises adjustment means (91) mounted in the connector (9) of the fixed frame and intended to lock/unlock the cutting unit (T) from the connector (9) and from the stem (41) and adjust the angle of the cutting unit (T) with respect to the handle (2) joined to the fixed frame.

As shown in FIGS. 8, 8A, 9, 9A, 10 and 10A, the connector (9) comprises a sleeve (95) disposed around the proximal end portions (31, 43) of the fixed beak and of the sliding tray.

The sleeve (95) comprises a radial rib (96) that radially protrudes inwards and a threaded hole (94) disposed in diametrally opposed direction with respect to the radial rib (96).

The proximal end portion (31) of the fixed beak has an annular groove (32) intended to be disposed in correspondence of the radial rib (96). In this way the radial rib (96) can be engaged inside the annular groove (32) in bayonet coupling mode, thus locking the movement of the cutting unit (T) with respect to the connector.

The adjustment means (91) comprise a knob (92) with a threaded stem (93) that is screwed in the threaded hole (94) of the sleeve of the connector. In this way the knob (92) can rotate around an axis orthogonal to the axis of translation of the sliding tray (4).

By rotating the knob (92), the threaded stem (93) is screwed in the threaded hole (94) of the sleeve. Consequently, the radial rib (96) of the sleeve of the connector is engaged in the annular groove (32) of the fixed beak or is released from the annular groove (32) of the fixed beak.

Figure 8:
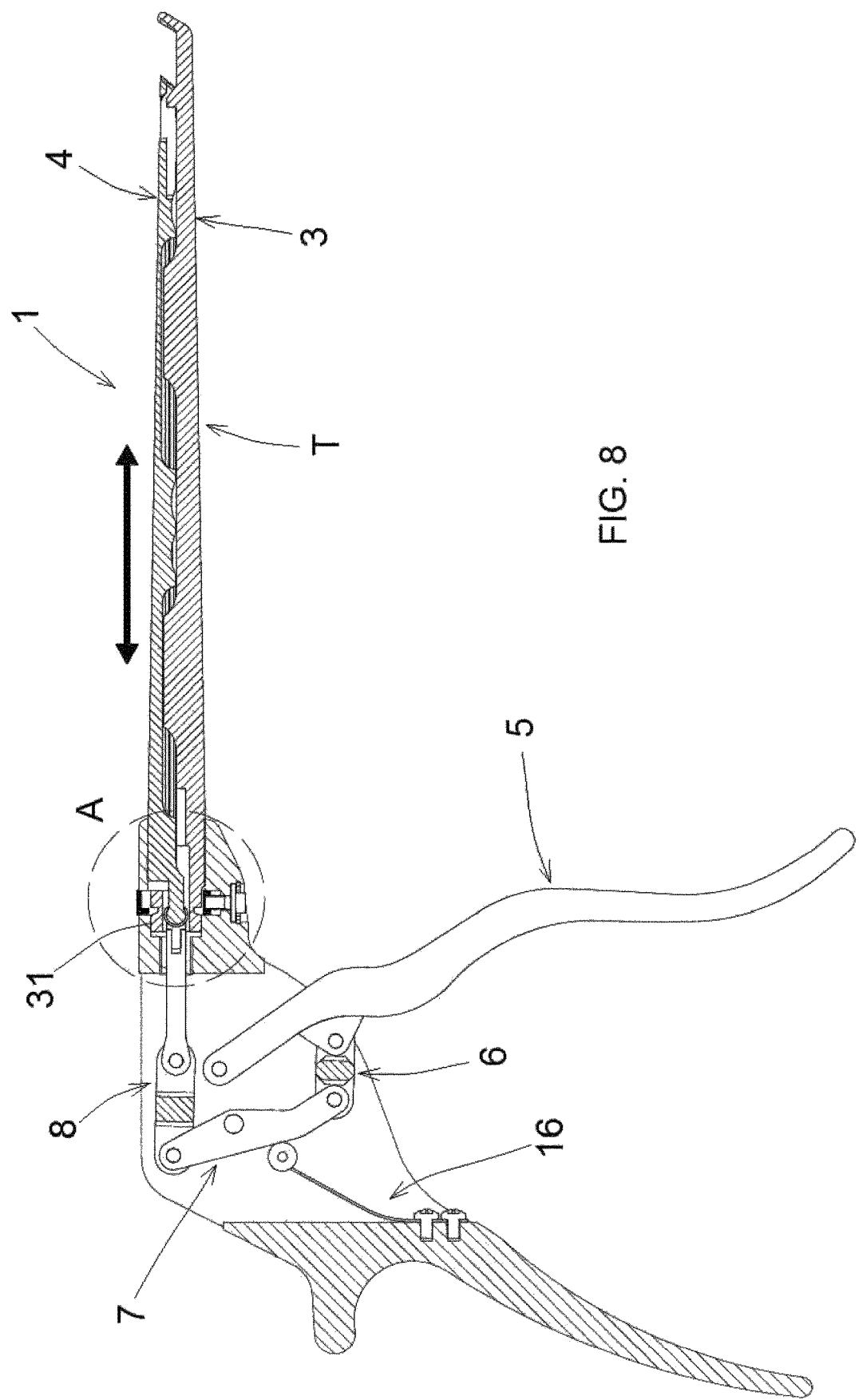
FIG. 8 is longitudinal sectional view of the forceps of FIG. 1, wherein the adjustment means are in such a position that they allow for extracting the cutting unit.
Figure 8A:
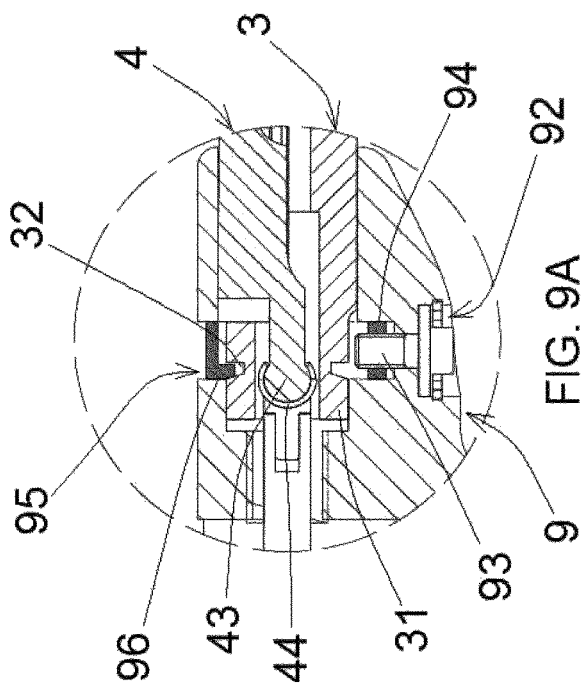
FIG. 8A is an enlarged view of the detail enclosed in the circle A of FIG. 8.

As shown in FIG. 8A, by unscrewing the knob (92), the rib (96) of the sleeve (95) comes out from the annular groove

(32) of the fixed beak, in such manner that the cutting unit (T) is not fixed to the connector (9) and can be extracted from the connector.

Figure 9A:
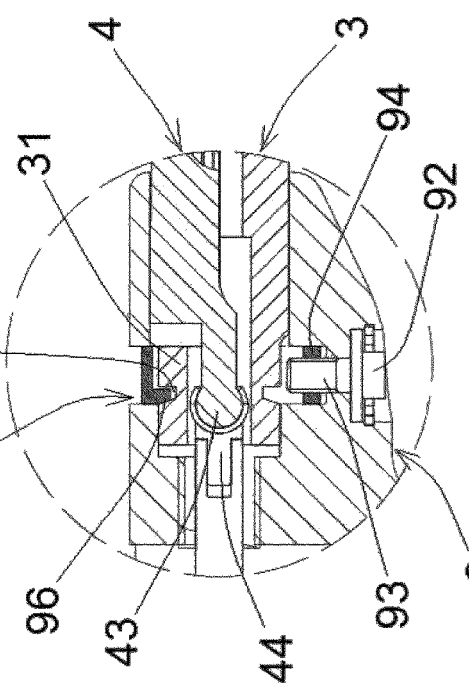
FIG. 9A is an enlarged view of the detail enclosed in the circle A of FIG. 9.

As shown in FIG. 9A, by slightly screwing the knob (92), the rib (96) of the sleeve (95) penetrates the annular groove (32) of the fixed beak, in such manner that the cutting unit (T) cannot be extracted from the fixed beak, In such a case, the cutting unit (T) can rotate around the longitudinal axis of the fixed beak, in such manner to change the angle of the cutting portion (30) and of the stop portion (40).

Figure 10A:
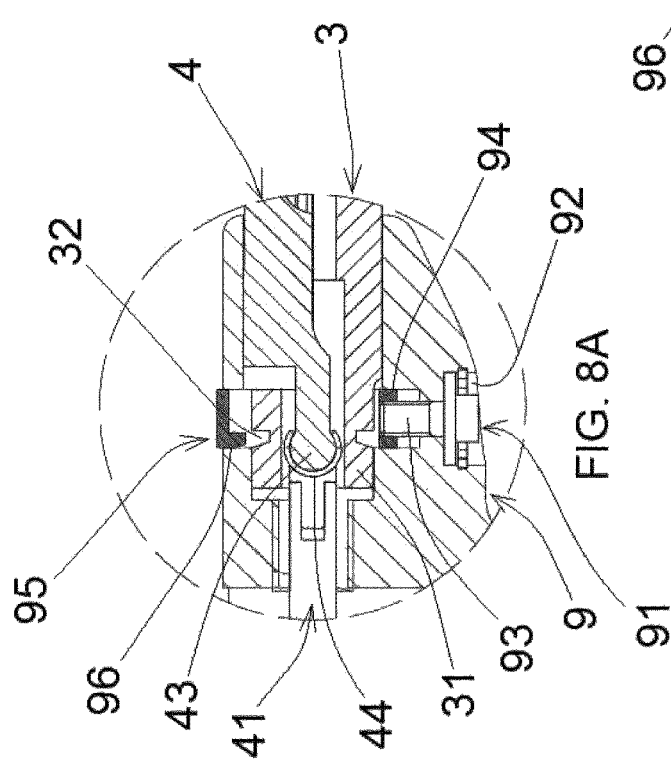
FIG. 10A is an enlarged view of the detail enclosed in the circle A of FIG. 10.
Figure 10:
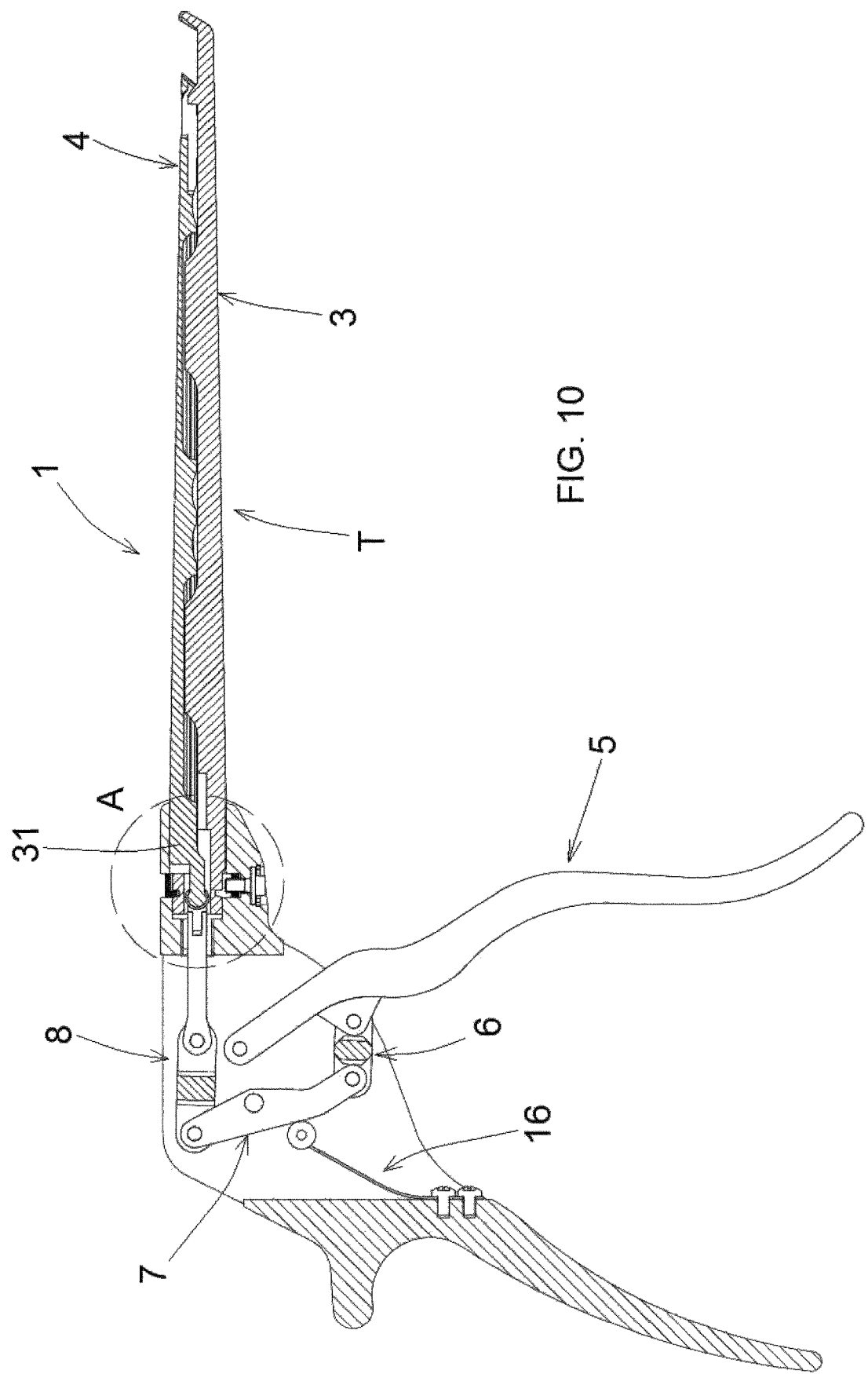
FIG. 10 is the same view as FIG. 8, except for the fact that the adjustment means are shown in a position in which they lock the cutting unit.

As shown in FIG. 10A, by forcedly screwing the stem (93) of the knob, the rib (96) of the sleeve (95) is forcedly tightened in the annular groove (32) of the fixed beak, in such manner that the cutting unit (T) is firmly fixed to the connector (9) and cannot rotate with respect to the connector (9).

Figure 11:
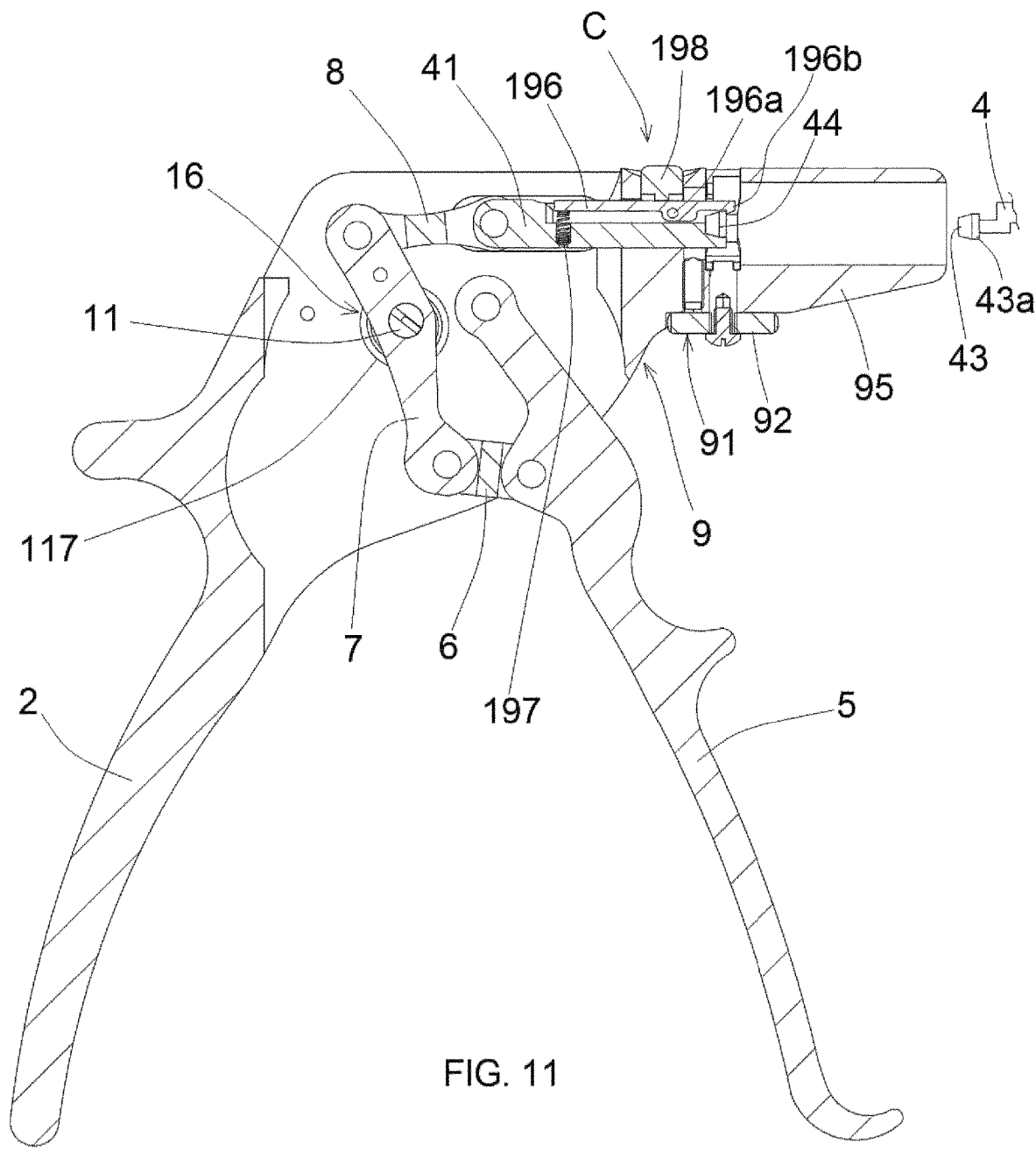
FIG. 11 is a partially interrupted sectional view of a variant of the forceps according to the invention.

With reference to FIG. 11 a variant of the forceps (1) of the invention is disclosed. In such a variant, the automatic return means (16) comprise a torsional spring (117) disposed around the fulcrum (11) of the second lever (7) to stress a rotation of the second lever (7) that pushes the actuation lever (5) to the opening position.

Such a variant of the forceps (1) of the invention provides for closing means (C) that can be manually actuated by the user to release the sliding tray (4) from the connector (9). In such a case, the proximal end portion (43) of the sliding tray has a truncated-conical shape and a stop surface (43a). The housing (44) of the stem (41) has a truncated-conical shape that is complementary to the shape of the proximal end portion (43) of the sliding tray.

The closing means (C) comprise a closing lever (196) that is hinged in a fulcrum (196a) to the connector (9). The lever has an end tooth (196b) intended to be engaged with a stop surface (43a) of the proximal end section (43) of the sliding tray, in such manner to hold and lock the sliding tray in the connector, A spring (197) acts on the closing lever (196) to maintain the closing lever in closing position. A button (198) protrudes in upper position from the connector (9) in order to be actuated by the operator and acts on the closing lever (196) to bring the closing lever to the opening position, wherein the end tooth (196b) releases the stop surface (43a) of the proximal end section of the sliding tray.

Figure 12:
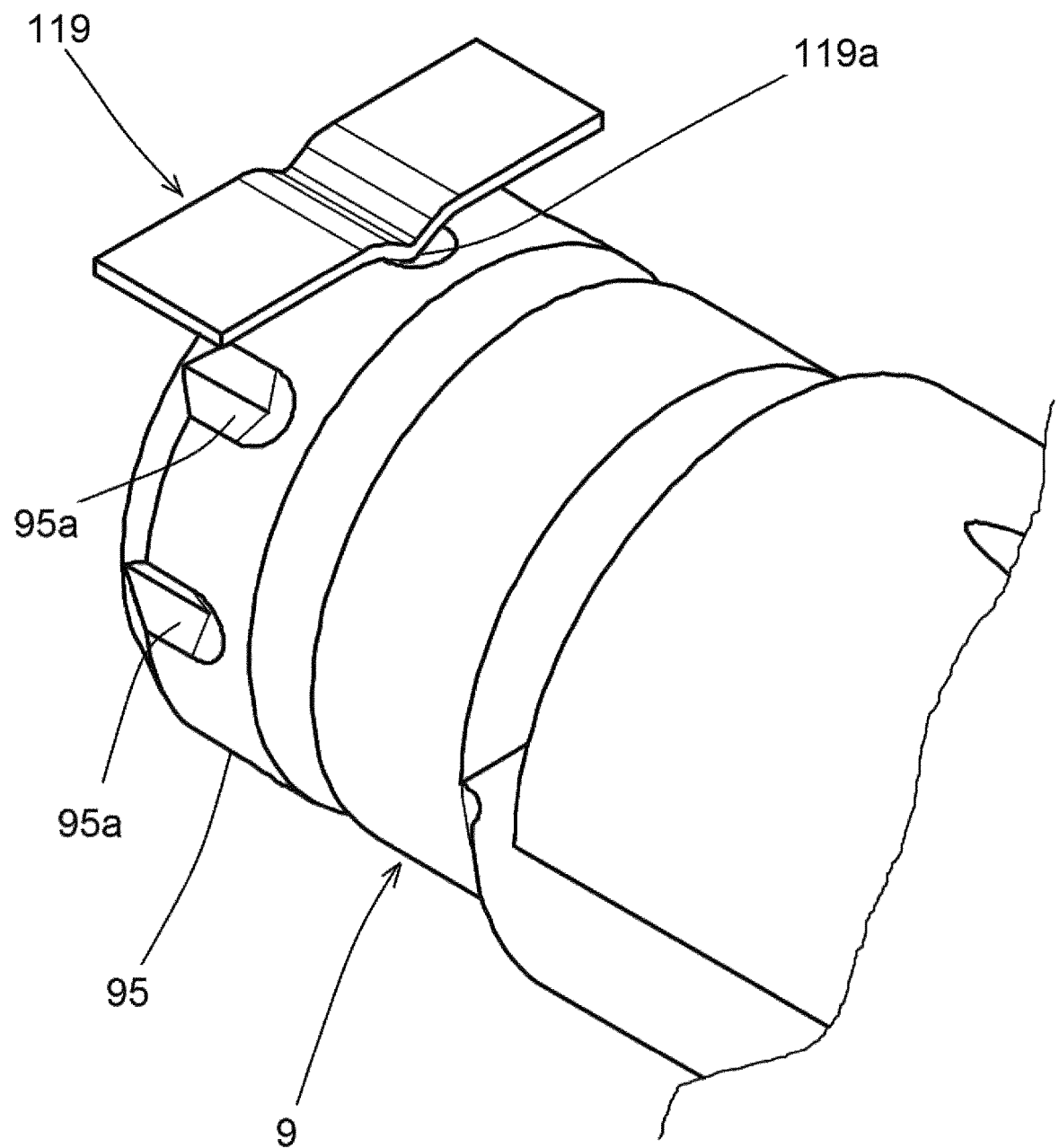
FIG. 12 is a partially interrupted perspective view of an additional variant of the forceps according to the invention.

With reference to FIG. 12 an additional variant of the forceps of the invention is disclosed. In such a case, the sleeve (95) of the connector (9) comprises a plurality of notches (95a) that are equally angularly-spaced around the sleeve (95). In the fixed frame (19) of the forceps a leaf spring (119) is mounted, having a tip (119a) that protrudes radially towards the sleeve (95) in order to be engaged in one of the notches (95a). In such a way, the rotation of the connector (9) can be adjusted and consequently the angular position of the cutting unit (T) of the forceps can be adjusted.

Now the operation of the forceps (1) of the invention is described. When the surgeon operates the actuation lever (5), moving the actuation lever closer to the handle (2), the actuation lever (5) is rotated around the pin (20), causing a translation of the first lever (6) towards the handle (2).

Consequently, the first arm of the second lever (7) is moved towards the handle (2) causing the rotation of the second lever (7) around the fulcrum (11). The second arm of the second lever (7) is moved towards the actuation lever (5) pushing the third lever (8) towards the beak (3), thus moving the sliding tray (4) in such manner to get the cutting portion (40) close to the stop portion (30).

When the surgeon releases the actuation lever (5), the return means (16) move the first arm of the second lever (7) towards the actuation lever (5). In such a way, the first lever (6) is moved towards the actuation lever (5) and consequently the actuation lever (5) is moved away from the handle (2).

Simultaneously, the second arm of the second lever (7) is moved towards the handle (2), also moving the third lever (8) towards the handle (2). The third lever (7) moves the stem (41) towards the handle (2), also moving the sliding tray (4). In such a way, the cutting portion (40) of the sliding tray (4) is moved away from the stop end (30) of the fixed beak (3).

In view of the above, the advantages of using such a lever mechanism are evident because, being shaped as a straight bar, said levers are easy to make, inexpensive and resistant.

Evidently, because of the provision of the adjustment means (91), it is possible to replace only the cutting unit when the cutting unit (30) and the stop portion (40) are worn out and have lost their sharp edge because of a prolonged used of the forceps, without having to replace the entire forceps.

Moreover, because of the provision of the adjustment means (91), the angle of the cutting unit (T) can be adjusted in such manner to reach points that are difficult or uncomfortable to reach.

The invention claimed is:

1. Laminectomy forceps comprising:
a cutting unit comprising a fixed beak and a sliding tray slidingly mounted on the fixed beak; said fixed beak comprising a stop portion intended to act as stop surface for a cutting portion of the sliding tray;
an actuation lever to actuate the sliding tray;
a lever mechanism connected to the actuation lever and to the sliding tray to multiply the force impressed on the actuation lever and transmit the multiplied force to the sliding tray;
a handle opposite to the actuation lever and joined to an external frame joined to the fixed beak;
wherein the force multiplicator lever mechanism comprises:
a first lever shaped as a straight bar and comprising a first end that is hinged to the actuation lever by means of a first pin and a second end that is hinged to a second lever by means of a second pin;
the second lever shaped as a straight bar revolvingly mounted around a fulcrum; the second lever being connected to the first lever by means of the second pin and to a third lever by means of a third pin;
the third lever shaped as a straight bar and comprising a first end that is hinged to the second lever by means of the third pin and a second end,
wherein
the fulcrum of the second lever is fixed to the external frame; the fulcrum is disposed between a first end of the second lever and a second end of the second lever in such manner to define:
a first arm between the fulcrum and the first end of the second lever connected to the first level; and
a second arm between the fulcrum and the second end of the second lever that is hinged to the third lever;
the second end of the third lever is connected by means of a fourth pin to a stem intended to push the sliding tray;
the first lever and the second lever form a first angle ($\alpha$) that is obtuse when the actuation lever is in opening position and becomes acute by actuating the actuation lever;

the second lever and the third lever form a second angle (β) that is acute when the actuation lever is in opening position and becomes obtuse by actuating the actuation lever;

the obtuse angles are in the range of 95° to 110° and the acute angles are in the range of 50° to 70°.

2. The forceps of claim 1, wherein the first lever and the third lever have an H-shaped longitudinal section and comprise two external walls connected by a central rib in such manner to define a first cavity in correspondence of the first end and a second cavity in correspondence of the second end.

3. The forceps of claim 2, wherein each external wall of the first lever and of the third lever has a through hole in correspondence of each cavity of the first lever and of the third lever; the first end of the second lever comprising a hole in concentric position to the holes in correspondence of the second end of the first lever and the second end of the second lever comprising a hole in concentric position to the holes in correspondence of the first end of the third lever.

4. The forceps of claim 1, wherein the second lever is longer than the first lever and the third lever is longer than the first lever and shorter than the second lever; said first arm of the second lever being longer than the second arm of the second lever.

5. The forceps of claim 1, wherein the actuation lever is configured in such manner to move with respect to the handle from an opening position, wherein the actuation lever is far apart from the handle and the cutting portion of the sliding tray is far away from the stop portion of the fixed beak, to a closing position, wherein the actuation lever is proximal to the handle and the cutting portion of the sliding tray is stopped against the stop portion of the fixed beak; said forceps comprising automatic return means intended to maintain the actuation lever in opening position.

6. The surgical forceps of claim 1, wherein:
the sliding tray comprises a proximal end portion intended to be removably attached to the stem connected to the lever mechanism, and
the fixed beak comprises a proximal end portion intended to be removably fixed in a connector joined to the fixed frame in such manner that the cutting unit can be released from the fixed frame.

7. The forceps of claim 6, wherein said proximal end portion of the sliding tray is a sphere intended to be coupled in a spherical housing obtained at one end of the stem (41) in such manner to form an omnidirectional spherical joint.

8. The forceps of claim 6, wherein said proximal end portion (43) of the sliding tray is truncated-conical and is intended to be engaged in a truncated-conical housing obtained at one end of said stem.

9. The forceps of claim 8, comprising closing means comprising:
a closing lever hinged in a fulcrum to the connector and having an end tooth intended to be engaged with a stop surface of the proximal end section of the sliding tray, in such manner to hold and lock the sliding tray in the connector,
a spring acting on the closing lever to maintain the closing lever in closing position, and
a button that protrudes in upper position from the connector in order to be actuated by the operator and acting on the closing lever to bring the closing lever to the opening position wherein the end tooth releases the stop surface of the proximal end section of the sliding tray.

10. The forceps of claim 6, wherein said connector is coupled with said proximal end portion of the fixed beak by means of bayonet coupling means.

11. The forceps of claim 6, comprising adjustment means mounted in said connector of the fixed frame and intended to lock/unlock the cutting unit to and from the connector and the stem, as well as to adjust the angle of the cutting unit with respect to the handle joined to the fixed frame, wherein said adjustment means comprise a knob that rotates around an axis that is orthogonal to the axis of translation of the sliding tray.

12. The forceps of claim 6, wherein the connector comprises a plurality of notches equally angularly-spaced around the connector, the forceps comprises a leaf spring fixed to the fixed frame and having a tip that protrudes radially towards the connector in order to be engaged in one of the notches.

* * * * *